(12) United States Patent
Kammerer et al.

(10) Patent No.: US 6,607,545 B2
(45) Date of Patent: Aug. 19, 2003

(54) CONFORMAL SURGICAL BALLOON WITH VARYING WALL EXPANSIBILITY

(75) Inventors: Gene W. Kammerer, East Brunswick, NJ (US); Dorothy Dion, West Orange, NJ (US); Martin Nohilly, Hoboken, NJ (US)

(73) Assignee: Ethicon, Inc., Somerville, NJ (US)

( * ) Notice: Subject to any disclaimer, the term of this patent is extended or adjusted under 35 U.S.C. 154(b) by 53 days.

(21) Appl. No.: 09/749,077

(22) Filed: Dec. 27, 2000

(65) Prior Publication Data

US 2002/0082634 A1 Jun. 27, 2002

(51) Int. Cl.$^7$ .............................................. A61M 29/00
(52) U.S. Cl. ..................................................... 606/193
(58) Field of Search ............................... 606/193, 192, 606/191, 27, 28, 41; 600/549

(56) References Cited

U.S. PATENT DOCUMENTS

| | | | |
|---|---|---|---|
| 5,449,380 A | * | 9/1995 | Chin ........................... 607/105 |
| 5,501,681 A | | 3/1996 | Neuwirth et al. |
| 5,891,457 A | | 4/1999 | Neuwirth et al. |
| 5,902,251 A | * | 5/1999 | Vanhooydonk ............. 600/549 |
| 5,954,714 A | * | 9/1999 | Saadat et al. .................. 606/28 |
| 5,964,755 A | * | 10/1999 | Edwards ........................ 606/41 |
| 6,026,331 A | | 2/2000 | Feldberg et al. |

OTHER PUBLICATIONS

Internet publication entitled "Innovation—Thermachoice® Uterine Balloon Therapy System", Johnson & Johnson, May 16, 2000 (http://www.jnj.com/innovations/in_thermachoice.html).

U.S. patent application Ser. No. 09/961,917, filed Sep. 24, 2001(As IDS #6).

U.S. patent application Ser. No. 09/749,180, filed Dec. 27, 2000.

* cited by examiner

Primary Examiner—Michael J. Milano
Assistant Examiner—Vy Q. Bui

(57) ABSTRACT

A surgical balloon for insertion into a body cavity with a major chamber having a first volume and an annexed minor chamber communicating therewith and having a second volume less than the first volume has a continuous outer wall which defines the exterior surface of the balloon on a first side and the interior hollow of the balloon on a second side. The wall is formed from a stretchable elastic material permitting the interior hollow of the balloon to accommodate a variable volume of fluid ranging from a minimum deflated volume associated with a relaxed state of the wall to a maximum inflated volume associated with a stretched state of the wall. The wall has selected areas of varying expansibility attributable to varying wall thickness, heat or chemical treatment. The wall provides the balloon with an inflated shape within the cavity approximating the interior shape of the body cavity, including a first portion approximating the major chamber and a second portion approximating the minor chamber. As applied to balloons for insertion into the uterus for endometrial ablation therapy, the balloon has a pair of projections for inserting into the uterine cornua. The balloon may be preformed to mimic the uterine shape in the deflated state, and may be formed from polyurethane promoting conformance of the inflated balloon to the uterine cavity.

8 Claims, 4 Drawing Sheets

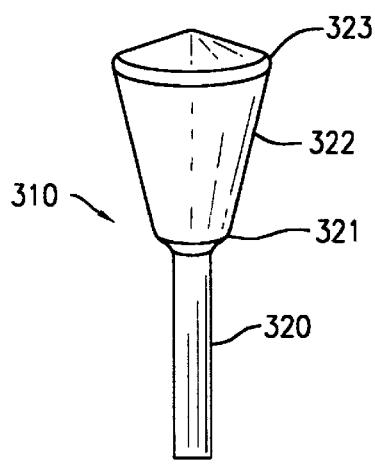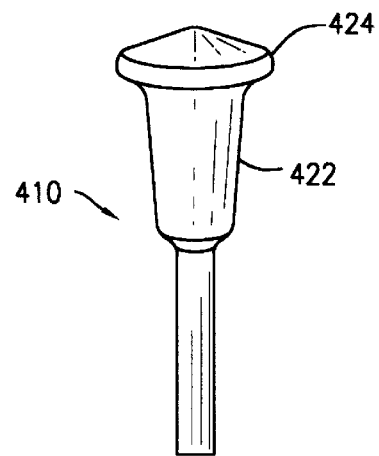
FIG. 7    FIG. 8
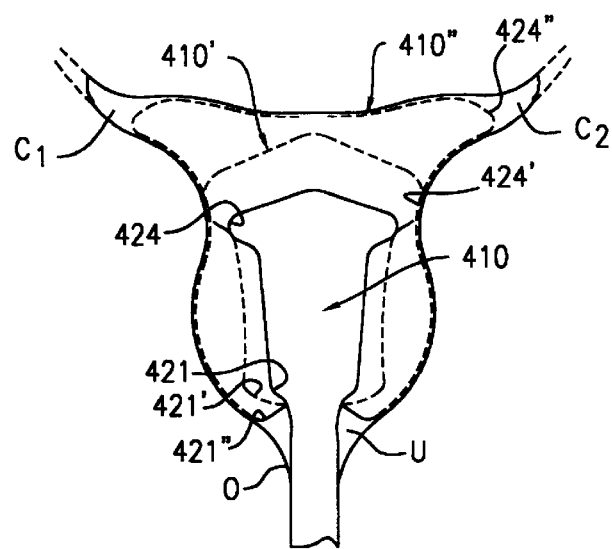
FIG. 9

CONFORMAL SURGICAL BALLOON WITH VARYING WALL EXPANSIBILITY

FIELD OF THE INVENTION

The present invention relates to surgical balloons, and more particularly to balloons suitable for introduction into a body cavity for containing a thermally conductive media used for ablation of cells within the cavity.

BACKGROUND OF THE INVENTION

Surgical balloons have a variety of uses, including the containment of fluids used to necrose cells lining a body cavity. For example, it has now become common to treat excessive menstrual bleeding (menorrhagia) by inserting a balloon catheter into the uterus, filling the balloon with a thermally conductive media and heating or cooling the media to thermally kill the endometrial lining of the uterus. An exemplary thermal ablation process and apparatus utilizing a surgical balloon are described in U.S. Pat. No. 5,502,681 to Neuwirth et al.

As shown in U.S. Pat. No. 5,502,681, known surgical balloons are typically formed from latex, have a bulb shape, and inflate in a manner which enlarges the bulb shape uniformly to an approximately spherical or bulbous shape. In contrast, the uterine cavity is Y-shaped in cross-section. The material composition of known balloons is somewhat inelastic, preventing the balloons from readily conforming to the intra-uterine space. As a result, known bulbous surgical balloons do not inflate to contact the entire endometrial lining, in particular, in the area of the uterine cornua. This lack of contact may result in a portion of the endometrial lining escaping treatment.

It is therefore an object of the present invention to provide an improved surgical balloon that exhibits an increased contact area with a body cavity into which it is inserted when the balloon is inflated.

SUMMARY OF THE INVENTION

The problems and disadvantages associated with the conventional surgical balloons are overcome by the present invention which includes a surgical balloon for to insertion into a body cavity with a major chamber having a first volume and an annexed minor chamber communicating therewith and having a second volume less than the first volume. The balloon has a continuous outer wall which defines the exterior surface of the balloon on a first side and the interior hollow of the balloon on a second side. The wall is formed from a stretchable elastic material permitting the interior hollow of the balloon to accommodate a variable volume of fluid ranging from a minimum deflated volume associated with a relaxed state of the wall to a maximum inflated volume associated with a stretched state of the wall. The wall has a varying expansibility permitting a selected portion thereof to expand further in the stretched state than the remainder of the wall. The wall provides the balloon with an inflated shape within the cavity approximating the interior shape of the body cavity, including a first portion approximating the major chamber and a second portion approximating the minor chamber.

BRIEF DESCRIPTION OF THE FIGURES

For a better understanding of the present invention, reference is made to the following detailed description of an exemplary embodiment considered in conjunction with the accompanying drawings, in which:

FIG. 7 is a plan view of a surgical balloon in accordance with an alternative exemplary embodiment of the present invention;

FIG. 8 is a plan view of a surgical balloon in accordance with another alternative embodiment of the present invention; and FIG. 9 is a diagrammatic view of the balloon of FIG. 8 at three stages of inflation within a uterine cavity.

DETAILED DESCRIPTION OF THE FIGURES

Figure 1:
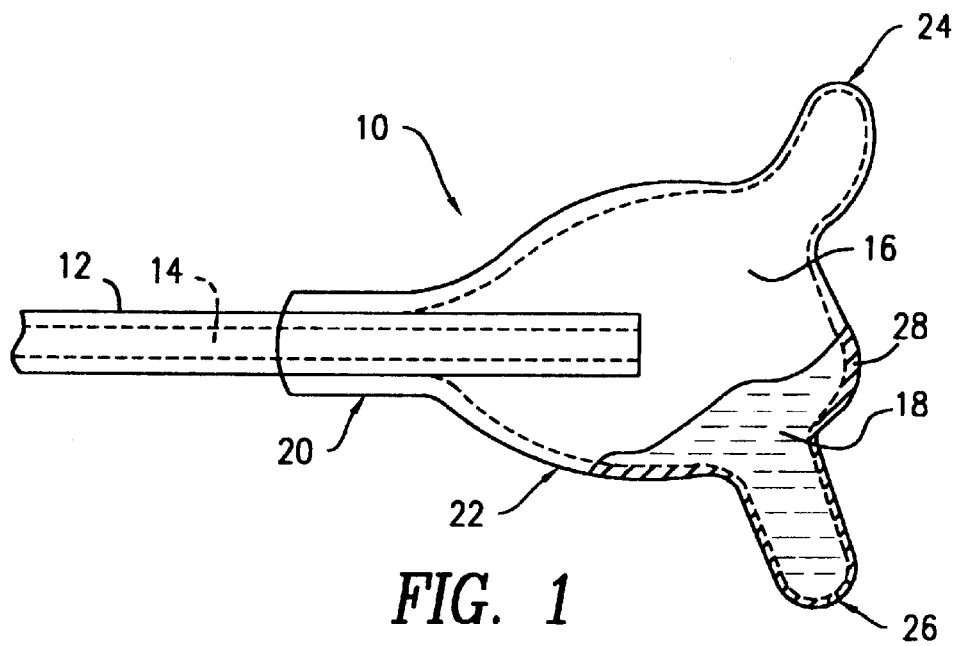
FIG. 1 is a plan view of an inflated surgical balloon in accordance with a first exemplary embodiment of the present invention.

FIG. 1 shows a surgical balloon 10 disposed on the end of a catheter 12. The catheter 12 has a lumen 14 that communicates with the interior hollow 16 of the balloon 12 and permits the infusion of a thermally conductive fluid 18 into the balloon 10 under pressure. As is known in the art, surgical balloons may be used to perform surgical procedures, such as endometrial ablation to cure menorrhagia. U.S. Pat. No. 5,954,714 is incorporated herein by reference for its teachings on the use of surgical balloons for endometrial ablation.

The balloon 10, as described herein, can be used in place of conventional bulb-shaped balloons to perform ablation procedures. More particularly, after the balloon 10 is introduced into the uterus, a pressurized thermally conductive fluid 18, e.g., saline solution, may be used to inflate the balloon 10 within the uterus, followed by heating or cooling of the fluid to thermally cauterize cells in contact with the balloon 10. The balloon 10 is preferably preformed to have a specific shape, such that when the balloon is inflated, it conforms to the walls of the intra-uterine space. The balloon 10 has a base 20 that is adhered to the catheter 12 by an adhesive or by plastic welding. The body 22 of the balloon 10 extends from the base 20 and has left and right extensions 24, 26. As can be appreciated from FIG. 1, the outer three-dimensional shape of the balloon 10 mimics the interior hollow of a uterus when the balloon 10 is inflated. In this manner, the balloon 10 of the present invention can more completely fill the hollow of the uterus into which it is inserted and contact a greater surface area relative to a bulb shaped balloon of the prior art. More particularly, the body 22 may extend from the isthmus to the fundus with the left and right extensions 24, 26 inserting into the uterine cornua. The greater contact area that may be achieved with the balloon 10 of the present invention provides for greater thermal transfer and more complete endometrial ablation.

FIG. 1 shows a portion of the wall 28 of the balloon 10 which has a varying thickness. More specifically, the balloon wall 28 is thick proximate the base 20 where it provides firm attachment to the catheter 12 and where it has no need to expand. The wall 28 is thinnest in those areas requiring maximum expansion, such as the extensions 24, 26, and of intermediate thickness in those areas requiring intermediate expansion, e.g., body 22. That is, in response to a given pressure, a thinner wall will expand outwardly more than a thicker wall. By varying the wall thickness, the balloon 10, which is bulb-shaped when deflated, can assume another shape, e.g., mimicking the intra-uterine space, when inflated. This shape transition of the balloon 10 occurs under the influence of the inherent expansion characteristics of the balloon 10, rather than in response to resistance to expansion exerted by the body cavity. Because the balloon 10 readily assumes a complementary shape to the body cavity in which it is placed, the balloon 10 conforms to the cavity shape without exerting as much pressure on the body cavity as conventional balloons. In addition, an even pressure is exerted by the balloon 10 across the internal surface of the uterus promoting consistent and even contact therebetween which translates to a uniform ablation depth of the cells.

As an alternative to or in addition to variations in wall thickness giving rise to local variations in expansibility, the wall 28 may be treated with heat, radiation or chemicals to achieve the same effect. More particularly, the balloon 10 can be made from polyurethane with a selected area exposed to heat in a temperature range of 260° F. to 280° F. by inserting the balloon 10 into an apertured mask made from aluminum or steel and exposing the balloon 10 to a heat source which will effect only the unmasked area. Alternatively, the balloon 10 may be installed upon a stretching frame and selected surfaces subsequently "branded" with heated dies. Alternatively, the balloon 10 may be stretched upon a frame and subjected to chemicals such as, dimethyl sulfoxide or tetrahydrofuran, that are printed on, brushed, dabbed or sprayed on through a mask.

The balloon 10 may be blow molded from polyester or polyethylene resins; dip molded from silicones, natural latex rubber or polyisoprene, a synthetic rubber; extrusion molded from silicone; injection molded from polyurethanes or silicones; or formed by heat sealing sections (patterns) together. Currently, the preferred method of manufacture is dip molding using natural latex rubber or polyisprene. Other compounds from which the balloon 10 can be made using one or more of the foregoing processes are polyether block amides, polyolefins and co-polyesters.

As referred to above, the balloon 10 can be formed by "heat sealing", viz., by cutting patterns of a sealable expandable material into specific shapes and then heat sealing the edges of the two identical shapes together. This can produce a structure, which has a volume between the top and bottom patterns. An alternate method is to place two sheets of material together, one on top of the other. A formed die is then placed on either side of the two sheets, and the die is heated to melt the sections of the sheets between the corresponding sections of the die. This area creates a seal when it cools. The shape or configuration of the die determines the shape of the balloon 10.

The balloon 10 of the present invention can be used in hot ablation procedures and in cryoablation. Materials, which are best suited for hot ablation procedures, would include polyisoprene, silicone and natural latex rubber. The material best suited for use in cold ablation procedures would be silicone.

Polyurethane, in contrast to the latex compounds that have previously been used to make surgical balloons, is highly elastic and permits the balloon 10 to conform readily to the intrauterine space, even with minimal or no variations in flexibility of the wall 28. Accordingly, the present invention is intended to include the use of polyurethane to produce a surgical balloon with either constant or varying wall thickness to insure low pressure conformation to the intrauterine shape.

Figure 2:
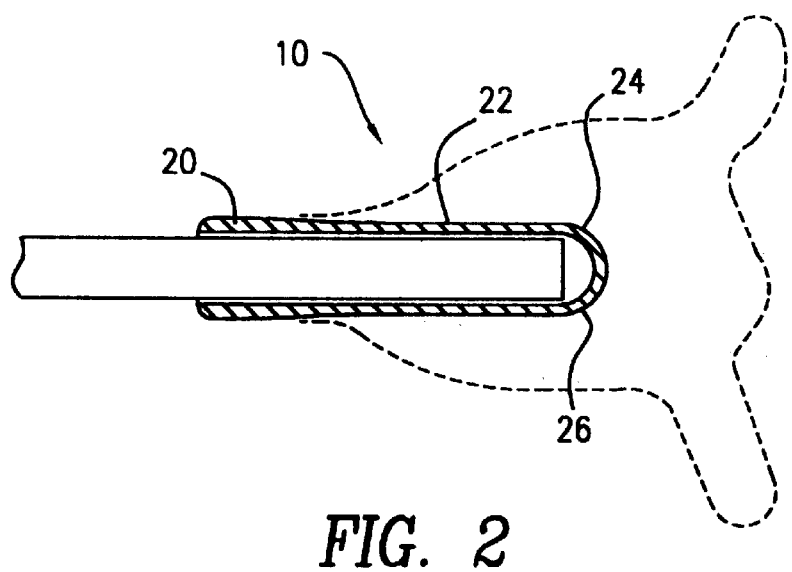
FIG. 2 is a cross-sectional view of the balloon of FIG. 1 in a deflated condition and showing the inflated condition in phantom.
Figure 3:
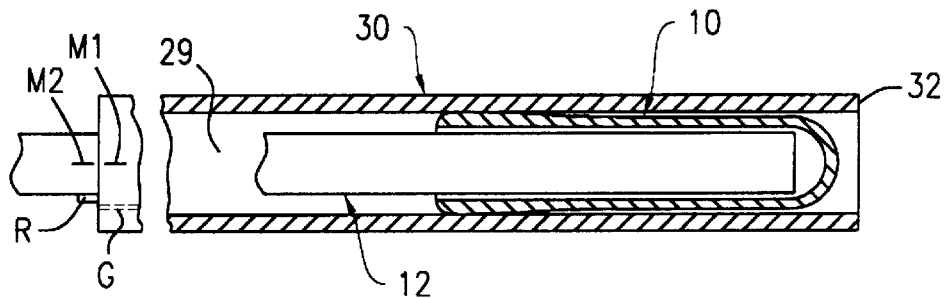
FIG. 3 is a cross-sectional view of the balloon of FIG. 2 stored within a cannula.

FIG. 2 illustrates the balloon 10 of FIG. 1 in a deflated state and the left and to right extensions 24, 26 appearing as internal surface indentations due to wall thinning in that area. The thickness of the wall 28 ramps down from the base 20 (which is thickest) to the body 22 (which is of intermediate thickness) and then to the extensions 24, 26 (which have the thinnest walls). It should be appreciated that the variation in the thickness of the wall 28 depicted in FIGS. 1, 2 and 3 is exaggerated for the purposes of illustration. In general, it is preferable for the thinning of the wall 28 to occur inside the balloon 10, in a symmetrical fashion. This will produce an even expansion of the outer surface. The transition from thin wall section to thick wall section will be smooth on the external surface of the balloon 10 in this configuration. Sharp changes in wall thickness will produce areas of high stress concentration, which will weaken the balloon 10 at those sites. This could lead to balloon failure during expansion.

As can be appreciated from FIG. 3, the deflated balloon 10 is readily accommodated within the lumen 29 of a cannula or introducer tube 30 that is used to facilitate introduction and deployment of the catheter 12 and balloon 10 into the uterus of a patient. More particularly, the cannula 30 can be slipped through the uterine os, followed by urging of the catheter 12 forward to deploy the balloon 10 beyond open tip 32 of the cannula 30. In the alternative, the cannula 30 can be withdrawn backward off of the balloon 10, exposing it in place. Once the balloon 10 is unconstrained by the cannula 30, it can be expanded under the influence of the infusion of thermally conductive fluid into the balloon 10, inflating it to the shape shown in FIG. 1.

A commonly owned copending application Serial No. 09/749,180 entitled "CONFORMAL SURGICAL BALLOON" and filed contemporaneously herewith by the present inventors, discloses a surgical balloon that conforms to the intra-uterine space aided by its preformed shape, such copending application being incorporated herein by reference. The present invention therefore contemplates a preformed surgical balloon (mimicking the uterine cavity shape) wherein the wall thickness and/or wall elasticity varies in accordance with the teachings of the present application, to aid in permitting the balloon to conform to the body cavity in which it is inflated. In particular, it is beneficial for the extensions 24, 26 of such a preformed balloon to have a thinner wall thickness and/or greater expansibility than the remainder of the balloon. Besides aiding the expansion of the extensions 24, 26 into the uterine cornua, the thinned extensions 24, 26 of a deflated preformed balloon can be more readily and compactly folded for storage within the cannula 30 and can be deployed more readily.

In the description to follow, a numbering convention will be used wherein elements having a similar function to a preceding embodiment shall have the same reference numerals increased by one hundred.

Figure 4:
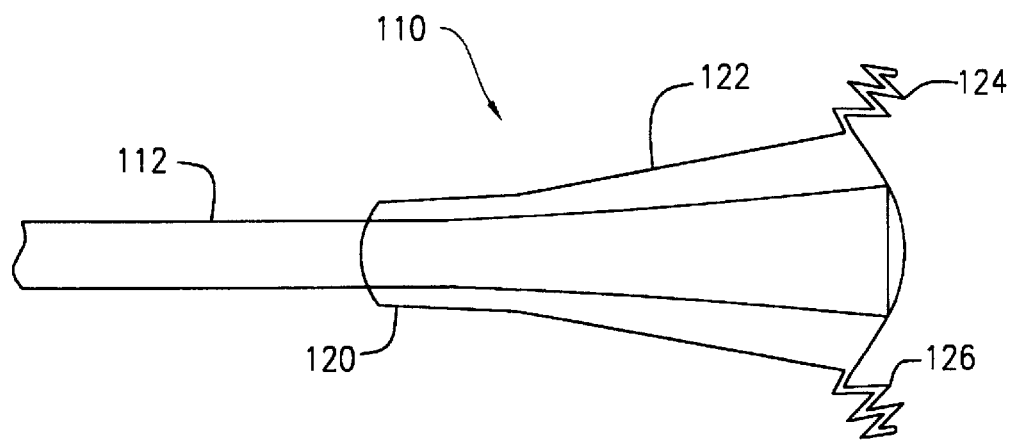
FIG. 4 is a plan view of an alternative embodiment of a balloon in accordance with the present invention.

FIG. 4 shows how a preformed balloon 110 with thinned extensions 124, 126 is folded to allow storage in the cannula 30 (see FIG. 3) and to facilitate a controlled unfolding and deployment when the balloon 110 is pushed out of the cannula 30 into the uterus. More specifically, the extensions 124, 126 are folded in a "zig-zag" configuration. Preferably, the balloon 110 is stored in a folded configuration that provides for a sequenced unfolding that properly positions the balloon 110 within the uterus to facilitate optimal balloon-to-endometrial lining contact when the thermally conductive media is infused into the balloon 110, inflating it and filling the intra-uterine space. When applied in the treatment of a body cavity having a directional sense, such as the uterus, the balloon 110 has a shape that requires orientation relative to the specific orientation of the body cavity in which it is deployed. The cannula 30 (see FIG. 3) and/or the catheter 112 are therefore preferably provided with an orientation marking $M_1$, $M_2$, respectively, that allows the surgeon to insert the balloon 10 in the proper orientation relative to the patient. To maintain the relative position of the catheter 112 and the cannula 30, it is preferred that each be keyed relative to the other, e.g., that the catheter 112 be provided with a longitudinal ridge R that fits within a mating guide way G in the cannula 30. In this manner, the orientation of the balloon 110 is preserved, while the balloon 110 is rotationally fixed relative to the cannula 30 and, in the case of a folded preformed balloon, avoiding inadvertently disturbing the folded position of the balloon 110.

The selection of material for the balloon 10, 110 insures that the balloon 10, 110 will not stick to itself or the cannula 30 after prolonged storage within the cannula 30. Alternatively, the balloon 10, 110 may be coated with a conventional biocompatible, non-allergenic lubricant, such as talc, cornstarch or low viscosity silicone, preferably air cured to prevent self-adhesion. In order to promote deployment of a folded balloon 110, it is preferably folded in a manner that minimizes overlap, severity of fold angle and compression forces that exceed the elastic limit of the material at fold lines. In addition, it is preferable that the extensions 124, 126 be folded at intervals that are smaller in length than the spacing between any opposed surfaces within the uterine cavity that could trap the extensions 124, 126 in an unfolded condition, e.g., between the walls of the uterine cornua or between the body of the balloon 110 and the uterine wall.

Figure 5:
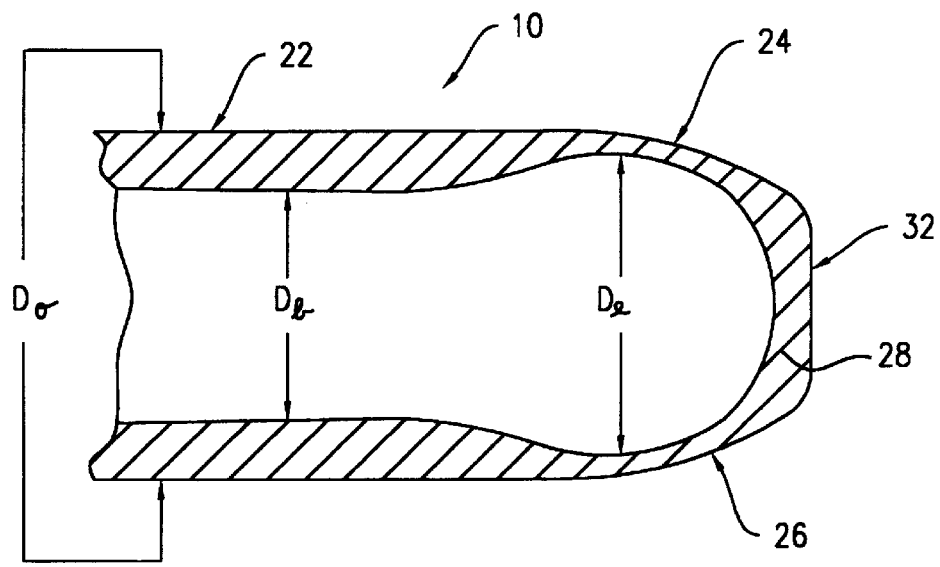
FIG. 5 is an enlarged, cross-sectional view of the tip of the deflated balloon of FIG. 1.

FIG. 5 shows a distal fragment of the balloon 10 of FIG. 3 illustrating how the wall 28 thickness may be selectively varied in accordance with the present invention. More to specifically, the thickness of the wall 28 at the tip 32 and body 22 portions is thinned in the area of the extensions 24, 26 by varying the internal diameter of the balloon 10 from $D_b$ to $D_e$ with the outer diameter $D_o$ remaining constant.

Figure 6:
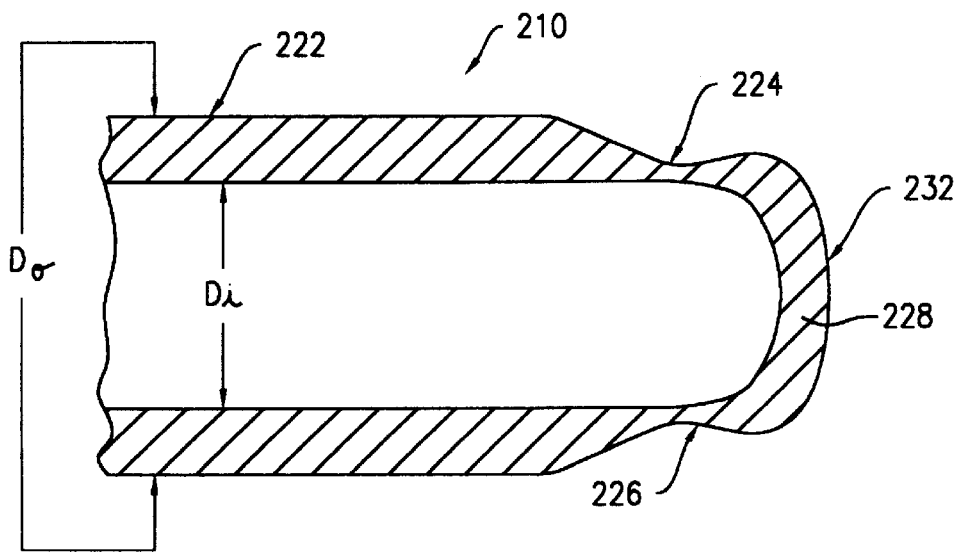
FIG. 6 is an enlarged, cross-sectional view of the tip of an alternative embodiment of the balloon of FIGS. 1 and 5 in accordance with the present invention.

FIG. 6 illustrates an alternative approach to that shown in FIG. 5, wherein the outer diameter $D_o$ of a balloon 210, decreases from that present on body 222 portion to a lesser diameter associated with extensions 224, 226, with the internal diameter $D_i$ remaining constant.

FIG. 7 shows a balloon 310 in accordance with the present invention and having an outwardly flaring body 322, the upper peripheral edge 323 of which is intended to extend into the uterine cornua of a patient. The body 322 is axially symmetric, i.e., generally bell-shaped. The shape of the balloon 310 can be determined by varying wall expansibility and/or pre-forming, such that the balloon 310 shown in FIG. 7 could be in the partially inflated state, i.e., having assumed that shape due to selected localized expansion characteristics of the wall of the balloon 310. Alternatively, the balloon 310 may be pre-formed, such that the shape shown is present when the balloon is inflated. In the case of a pre-formed balloon 310 having an uninflated shape as shown, variations in wall expansibility may be incorporated therein in order to further assist the balloon 310 in conforming to the body cavity when it is more fully inflated. When inflated, the overall shape of the balloon 310 and corresponding distribution of flexible wall material allows the upper peripheral edge 323 to expand out into the cornua. The body 322 flares out rapidly from the base 320 to a lower circumference 321 to increase contact with the uterus proximate the uterine os. This effect is illustrated in FIG. 9 described below:

FIG. 8 shows a balloon 410 having a shape similar to the balloon 310 of FIG. 6, but with an expandable upper flange 424 to facilitate expansion into the uterine cornua. FIG. 9 illustrates the balloon 410 within a uterine cavity U, in the uninflated state, in an intermediate state of inflation 410' (dotted) and inflated almost completely 410" (dotted). As the balloon 410 is inflated, the expansible flange 424, (424', 424") approaches and enters the uterine cornua $C_1$, $C_2$. Simultaneously, lower circumference 421, (421', 421") immediately expands outwardly to contact the uterine cavity U proximate the os O. Depending upon the shape of the uterine cavity U, the lower circumference 421" may project downwardly to fill the space between the base 420 and the uterine cavity U proximate the os O. Alternatively, the expansion of the balloon 410 will push the base 420 in an outward direction (to a lesser degree of insertion) such that the balloon 410 will establish maximum contact with the uterine cavity U. Accordingly, surgical balloons 10, 110, 210, 310, 410 establish greater contact with the uterine cavity U more quickly and completely than a conventional bulb-shaped balloon. Since the balloons 10, 110, 210, 310, 410 more readily inflate to a shape approximating the cavity into which they are inserted, greater contact area at a more even, higher pressure is achieved, assuring better thermal transfer.

It should be appreciated that the present invention contemplates a balloon 10, 110, 210, 310, 410 with a symmetrical radial thinning or treatment such that the thinned area, if inflated outside the body, would assume a toroidal, radially symmetric shape. If the same balloon were inflated within the body, e.g., the uterus, then the thinned area would be constrained by the cavity shape such that the extensions 24, 26 (224, 226) can extend into the uterine cornua. Under such circumstances, the balloon will be radially symmetric such that there is no need to provide a means to radially align the balloon to the uterus.

Alternatively, the thinning or treatment of the balloon 10, 110, 210 may be localized such that the extensions 24, 26 (124, 126 and 224, 226) project out like fingers. In that case, the alignment means referred to above in reference to FIG. 4 is preferred in order to align the balloon 10, 110, 210 to the body cavity.

It should be understood that the embodiments described herein are merely exemplary and that a person skilled in the art may make many variations and modifications without departing from the spirit and scope of the invention as defined in the appended claims. All such variations and modifications are intended to be included within the scope of the present invention as defined in the appended claims.

We claim:

1. A surgical balloon for insertion into a uterus with a primary uterine space extending between the os and the fundus having a first volume and two annexed cornua communicating therewith and having a second and third volume, respectively, each less than the first volume, comprising:

a continuous outer wall, said wall defining an exterior surface of said balloon on a first side and an interior hollow of said balloon on a second side, said wall being formed from a stretchable elastic material permitting said interior hollow of said balloon to accommodate a variable volume of fluid ranging from a minimum deflated volume associated with a relaxed state of said wall to a maximum inflated volume associated with a stretched state of said wall, said wall having a varying expansibility permitting first and second portions of said wall to expand further in said stretched state than a remainder of said wall, said wall providing the balloon with an inflated shape within the uterus approximating the interior shape thereof, said remainder approximating the primary uterine space, said first portion approximating a first of the two annexed cornua and said second portion approximating a second of the two annexed cornua, said first and second portions of said wall being thinner than said remainder of said wall.

2. The surgical balloon of claim 1, further including a catheter having a lumen for conducting a fluid therethrough, said balloon sealingly attached to said catheter at one end thereof with said lumen in communication with the interior hollow of the balloon.

3. The surgical balloon of claim 2, further including a cannula to aid in introducing said balloon into the uterus, said balloon and said catheter being slidably and removably contained within said cannula.

4. The surgical balloon of claim 3, wherein said cannula has an orientation marking thereon to permit a user thereof to ascertain the orientation of said balloon contained therein.

5. The surgical balloon of claim 4, further including alignment means for maintaining said cannula and said catheter in relative alignment when said catheter is stored within said cannula.

6. The surgical balloon of claim 1, wherein said wall is made of polyurethane.

7. The surgical balloon of claim 1, wherein said wall is a material selected from the group consisting of polyurethane, latex, polyester, polyethylene, silicone and polyisoprene.

8. The surgical balloon of claim 2, wherein said balloon flares outwardly from said catheter to a first diameter to facilitate said balloon approximating said primary uterine space proximate an os of the uterus into which said balloon is introduced.

* * * * *